United States Patent
Weising

(10) Patent No.: US 8,484,219 B2
(45) Date of Patent: Jul. 9, 2013

(54) DEVELOPING A KNOWLEDGE BASE ASSOCIATED WITH A USER THAT FACILITATES EVOLUTION OF AN INTELLIGENT USER INTERFACE

(75) Inventor: George Weising, Culver City, CA (US)

(73) Assignee: Sony Computer Entertainment America LLC, Foster City, CA (US)

( * ) Notice: Subject to any disclaimer, the term of this patent is extended or adjusted under 35 U.S.C. 154(b) by 229 days.

(21) Appl. No.: 12/887,511

(22) Filed: Sep. 22, 2010

(65) Prior Publication Data

US 2012/0072424 A1   Mar. 22, 2012

Related U.S. Application Data

(63) Continuation-in-part of application No. 12/887,397, filed on Sep. 21, 2010.

(51) Int. Cl.
*G06F 7/00* (2006.01)
*G06F 17/30* (2006.01)
*G06F 19/00* (2011.01)
*G06F 7/08* (2006.01)

(52) U.S. Cl.
CPC .............. *G06F 19/707* (2013.01); *G06F 7/08* (2013.01); *G06F 17/30412* (2013.01); *G06F 17/30598* (2013.01); *Y10S 707/948* (2013.01)
USPC ............................ 707/740; 707/805; 707/948

(58) Field of Classification Search
CPC ..... G06F 19/707; G06F 7/08; G06F 17/30412; G06F 17/30598
USPC .................. 707/737, 740, 948, 805
See application file for complete search history.

(56) References Cited

U.S. PATENT DOCUMENTS

| | | |
|---|---|---|
| 3,409,877 A | 11/1968 | Alterman et al. |
| 3,436,734 A | 4/1969 | Pomerene et al. |
| 3,517,171 A | 6/1970 | Avizienis |
| 3,623,014 A | 11/1971 | Doelz et al. |
| 3,668,644 A | 6/1972 | Looschen |
| 4,485,457 A | 11/1984 | Balaska et al. |
| 4,587,640 A | 5/1986 | Saitoh |
| 4,752,068 A | 6/1988 | Endo |
| 4,858,930 A | 8/1989 | Sato |

(Continued)

FOREIGN PATENT DOCUMENTS

| | | |
|---|---|---|
| EP | 0454340 | 10/1991 |
| EP | 0773490 | 5/1997 |

(Continued)

OTHER PUBLICATIONS

Mueller et al., "A Nested Transaction Mechanisum for LOCUS," Proceedings of the Ninth ACM Symposium on Operating System Principles (1983).

*Primary Examiner* — Phong Nguyen
(74) *Attorney, Agent, or Firm* — Carr & Ferrell LLP

(57) ABSTRACT

Developing a knowledgebase associated with a user interface is disclosed. Development of the knowledgebase includes cataloging local data associated with a user, collecting remote data associated with the user, recording information associated with verbal input received from the user, tracking acts performed by the user to determine user idiosyncrasies, and updating the knowledgebase with the cataloged local data, the collected remote data, the recorded information, and the user idiosyncrasies. The updated knowledgebase is then provided to a component of a user interface.

46 Claims, 9 Drawing Sheets

U.S. PATENT DOCUMENTS

| | | |
|---|---|---|
| 5,014,982 A | 5/1991 | Okada et al. |
| 5,128,863 A | 7/1992 | Nakamura et al. |
| 5,222,134 A | 6/1993 | Waite et al. |
| 5,233,423 A | 8/1993 | Jernigan et al. |
| 5,273,294 A | 12/1993 | Amanai |
| 5,477,492 A | 12/1995 | Ohsaki et al. |
| 5,490,216 A | 2/1996 | Richardson, III |
| 5,523,551 A | 6/1996 | Scott |
| 5,532,735 A | 7/1996 | Blahut et al. |
| 5,636,277 A | 6/1997 | Nagahama |
| 5,729,214 A | 3/1998 | Moore |
| 5,794,217 A | 8/1998 | Allen |
| 5,809,145 A | 9/1998 | Slik et al. |
| 5,829,047 A | 10/1998 | Jacks et al. |
| 5,838,314 A | 11/1998 | Neel et al. |
| 5,892,900 A | 4/1999 | Ginter et al. |
| 5,913,040 A | 6/1999 | Rakavy et al. |
| 5,971,856 A | 10/1999 | Aoyama et al. |
| 6,066,182 A | 5/2000 | Wilde et al. |
| 6,070,141 A | 5/2000 | Houvener et al. |
| 6,073,123 A | 6/2000 | Staley |
| 6,081,785 A | 6/2000 | Oshima et al. |
| 6,085,262 A | 7/2000 | Sawada |
| 6,117,011 A | 9/2000 | Lvov |
| 6,119,108 A | 9/2000 | Holmes et al. |
| 6,135,646 A | 10/2000 | Kahn et al. |
| 6,137,480 A | 10/2000 | Shintani |
| 6,148,335 A | 11/2000 | Haggard et al. |
| 6,189,146 B1 | 2/2001 | Misra et al. |
| 6,195,432 B1 | 2/2001 | Takahashi et al. |
| 6,201,771 B1 | 3/2001 | Otsuka et al. |
| 6,243,796 B1 | 6/2001 | Otsuka |
| 6,247,131 B1 | 6/2001 | Kotani et al. |
| 6,260,141 B1 | 7/2001 | Park |
| 6,311,209 B1 | 10/2001 | Olson et al. |
| 6,314,451 B1 | 11/2001 | Landsman et al. |
| 6,405,203 B1 | 6/2002 | Collart |
| 6,434,535 B1 | 8/2002 | Kupka et al. |
| 6,446,260 B1 | 9/2002 | Wilde et al. |
| 6,463,078 B1 | 10/2002 | Engstrom et al. |
| 6,470,085 B1 | 10/2002 | Uranaka et al. |
| 6,529,453 B1 | 3/2003 | Otsuka et al. |
| 6,560,640 B2 | 5/2003 | Smethers |
| 6,571,211 B1 * | 5/2003 | Dwyer et al. ............... 704/270 |
| 6,594,740 B1 | 7/2003 | Fukuda |
| 6,611,607 B1 | 8/2003 | Davis et al. |
| 6,640,306 B1 | 10/2003 | Tone et al. |
| 6,694,025 B1 | 2/2004 | Epstein et al. |
| 6,811,490 B2 | 11/2004 | Rubin |
| 6,832,318 B1 | 12/2004 | Yaegashi et al. |
| 6,920,565 B2 | 7/2005 | Isaacson et al. |
| 7,071,914 B1 | 7/2006 | Marks |
| 7,263,462 B2 | 8/2007 | Funge |
| 7,296,007 B1 | 11/2007 | Funge |
| 7,313,251 B2 | 12/2007 | Rhoads |
| 7,363,384 B2 | 4/2008 | Chatani et al. |
| 7,425,903 B2 | 9/2008 | Boss et al. |
| 7,426,750 B2 | 9/2008 | Cooper et al. |
| 7,440,431 B2 | 10/2008 | Sindhushayana et al. |
| 7,466,241 B2 | 12/2008 | Lyle et al. |
| 7,495,631 B2 | 2/2009 | Bhakta et al. |
| 7,558,698 B2 | 7/2009 | Funge |
| 7,636,645 B1 | 12/2009 | Yen |
| 7,636,697 B1 | 12/2009 | Dobson |
| 7,636,701 B2 | 12/2009 | Funge |
| 7,703,611 B1 * | 4/2010 | Appelman et al. ............ 209/206 |
| 8,112,407 B2 * | 2/2012 | Jung et al. ............... 707/706 |
| 8,126,867 B2 * | 2/2012 | Jung et al. ............... 707/706 |
| 2001/0020295 A1 | 9/2001 | Satoh |
| 2001/0025256 A1 | 9/2001 | Oliphant et al. |
| 2001/0034721 A1 | 10/2001 | Boudreau et al. |
| 2001/0042021 A1 | 11/2001 | Matsuo et al. |
| 2001/0051996 A1 * | 12/2001 | Cooper et al. ............... 709/217 |
| 2002/0016922 A1 | 2/2002 | Richards et al. |
| 2002/0052816 A1 | 5/2002 | Clenaghan et al. |
| 2002/0077988 A1 | 6/2002 | Sasaki et al. |
| 2002/0082997 A1 | 6/2002 | Kobata et al. |
| 2002/0103855 A1 | 8/2002 | Chatani |
| 2002/0104019 A1 | 8/2002 | Chatani et al. |
| 2002/0116206 A1 | 8/2002 | Chatani |
| 2002/0116283 A1 | 8/2002 | Chatani |
| 2002/0129094 A1 | 9/2002 | Reisman |
| 2002/0142845 A1 | 10/2002 | Randall Whitten et al. |
| 2002/0161709 A1 | 10/2002 | Floyd et al. |
| 2003/0032486 A1 | 2/2003 | Elliott |
| 2005/0071328 A1 * | 3/2005 | Lawrence ............... 707/3 |
| 2006/0264259 A1 | 11/2006 | Zalewski et al. |
| 2007/0015558 A1 | 1/2007 | Zalewski et al. |
| 2007/0015559 A1 | 1/2007 | Zalewski et al. |
| 2007/0021208 A1 | 1/2007 | Mao et al. |
| 2007/0082706 A1 * | 4/2007 | Campbell et al. ............ 455/563 |
| 2007/0168359 A1 | 7/2007 | Jacob et al. |
| 2007/0168462 A1 * | 7/2007 | Grossberg et al. ............ 709/217 |
| 2007/0243930 A1 | 10/2007 | Zalewski et al. |
| 2007/0244751 A1 | 10/2007 | Zalewski et al. |
| 2007/0255630 A1 | 11/2007 | Zalewski et al. |
| 2007/0261077 A1 | 11/2007 | Zalewski et al. |
| 2008/0015878 A1 * | 1/2008 | Feng et al. ............... 705/1 |
| 2008/0024722 A1 | 1/2008 | Pollard |
| 2008/0098448 A1 | 4/2008 | Mondesir et al. |
| 2008/0189170 A1 * | 8/2008 | Ramachandra ............... 705/10 |
| 2008/0253740 A1 | 10/2008 | Rhoads |
| 2009/0112810 A1 * | 4/2009 | Jung et al. ............... 707/3 |
| 2009/0112914 A1 * | 4/2009 | Jung et al. ............... 707/102 |
| 2009/0221368 A1 | 9/2009 | Yen |
| 2009/0221374 A1 | 9/2009 | Yen |
| 2009/0288064 A1 | 11/2009 | Yen |
| 2010/0004896 A1 | 1/2010 | Yen |
| 2010/0262924 A1 * | 10/2010 | Kalu ............... 715/753 |
| 2011/0035265 A1 * | 2/2011 | King et al. ............... 705/14.13 |

FOREIGN PATENT DOCUMENTS

| | | |
|---|---|---|
| EP | 0795809 | 9/1997 |
| EP | 1016960 | 7/2000 |
| JP | 04253885 | 9/1992 |
| JP | 06180674 | 6/1994 |
| JP | 9244886 | 9/1997 |
| JP | 10069511 | 3/1998 |
| JP | 10133955 | 5/1998 |
| JP | 10222428 | 8/1998 |
| JP | 11143719 | 5/1999 |
| JP | 2000020795 | 1/2000 |
| JP | 2000227919 | 8/2000 |
| JP | 2000298689 | 10/2000 |
| JP | 2001169246 | 6/2001 |
| KR | 1998030143 | 7/1998 |
| KR | 1998033266 | 7/1998 |
| KR | 2000060715 | 10/2000 |
| WO | 00/63860 | 10/2000 |
| WO | 02/01333 | 1/2002 |

* cited by examiner

DEVELOPING A KNOWLEDGE BASE ASSOCIATED WITH A USER THAT FACILITATES EVOLUTION OF AN INTELLIGENT USER INTERFACE

CROSS REFERENCE TO RELATED APPLICATIONS

This application is a continuation in part and claims the priority benefit of U.S. patent application Ser. No. 12/887,397 filed Sep. 21, 2010 and entitled "Evolution of a User Interface Based on Learned Idiosyncrasies and Collected Data of a User," the disclosure of which is incorporated herein by reference.

BACKGROUND OF THE INVENTION

1. Field of the Invention

The present invention generally relates to user interfaces. More specifically, the present invention relates to developing a knowledge base associated with a user and that facilitates evolution of an intelligent user interface that evolves based on learned idiosyncrasies and collected data of a user.

2. Description of the Related Art

A user interface is an aggregate of means by which people—users—interact with a system such as a particular machine, device, computer program, or other complex tool. The user interface provides means of input and output. The input means allow the user to manipulate the system, while the output means allow the system to indicate the effects of the user manipulation. The design of a user interface affects the amount of effort a user must expend to provide input for the system and to interpret output of the system. Usability is the degree to which the design of a particular user interface takes into account the human psychology and behavioral characteristics of the users, and makes the process of using the system effective, efficient and satisfying.

Current user interfaces are, at best, minimally personalized. Generally, these user interfaces are available with factory-set defaults that are selected with the general population or another large user group in mind. Users may be provided with the option of changing certain preferences; however any preference changes will be limited to a predefined list thereof. Furthermore, any customized behavior of these user interfaces must be specifically programmed by the user or otherwise. Given these and other limitations with current user interfaces, what is needed is a user interface that evolves in various aspects during use based on characteristics, habits, and other data associated with a user.

SUMMARY OF THE CLAIMED INVENTION

Embodiments of the present invention develop a knowledge base associated with a user that facilitates evolution of an intelligent user interface.

A claimed embodiment recites developing a knowledgebase associated with a user interface. The method includes executing instructions stored in memory to catalog local data associated with a user, collect remote data associated with the user, record information associated with verbal input received from the user, track acts performed by the user to determine user idiosyncrasies, and update the knowledgebase with the cataloged local data, the collected remote data, the recorded information, and the user idiosyncrasies. The method further includes providing the updated knowledgebase to a component of the user interface.

DETAILED DESCRIPTION

Embodiments of the presently disclosed invention allow an intelligent user interface to be provided that evolves based on learned idiosyncrasies and collected data of a user. As the user interacts with the intelligent user interface, idiosyncrasies of the user such as habits and rituals will be learned. Additionally, data associated with the user will be collected from local and remote sources. Examples of local data include a catalog of user media or services available to a system presenting the user interface. Examples of remote data include an index of information from third-party accounts associated with the user or textual communication by the user. Further information can be obtained through interactive dialog with the user in which the user explicitly or implicitly provides the information thought verbal input.

The sum of obtained information associated with the user—both local and remote—can be stored in a regularly-updated knowledge base and be used to generate thought-based statements. The thought-based statements serve to invoke or respond to subsequent actions of the user. Though this iterative process of "getting to know" the user, the user interface evolves to better satisfy the wants and needs of the user.

Figure 1:
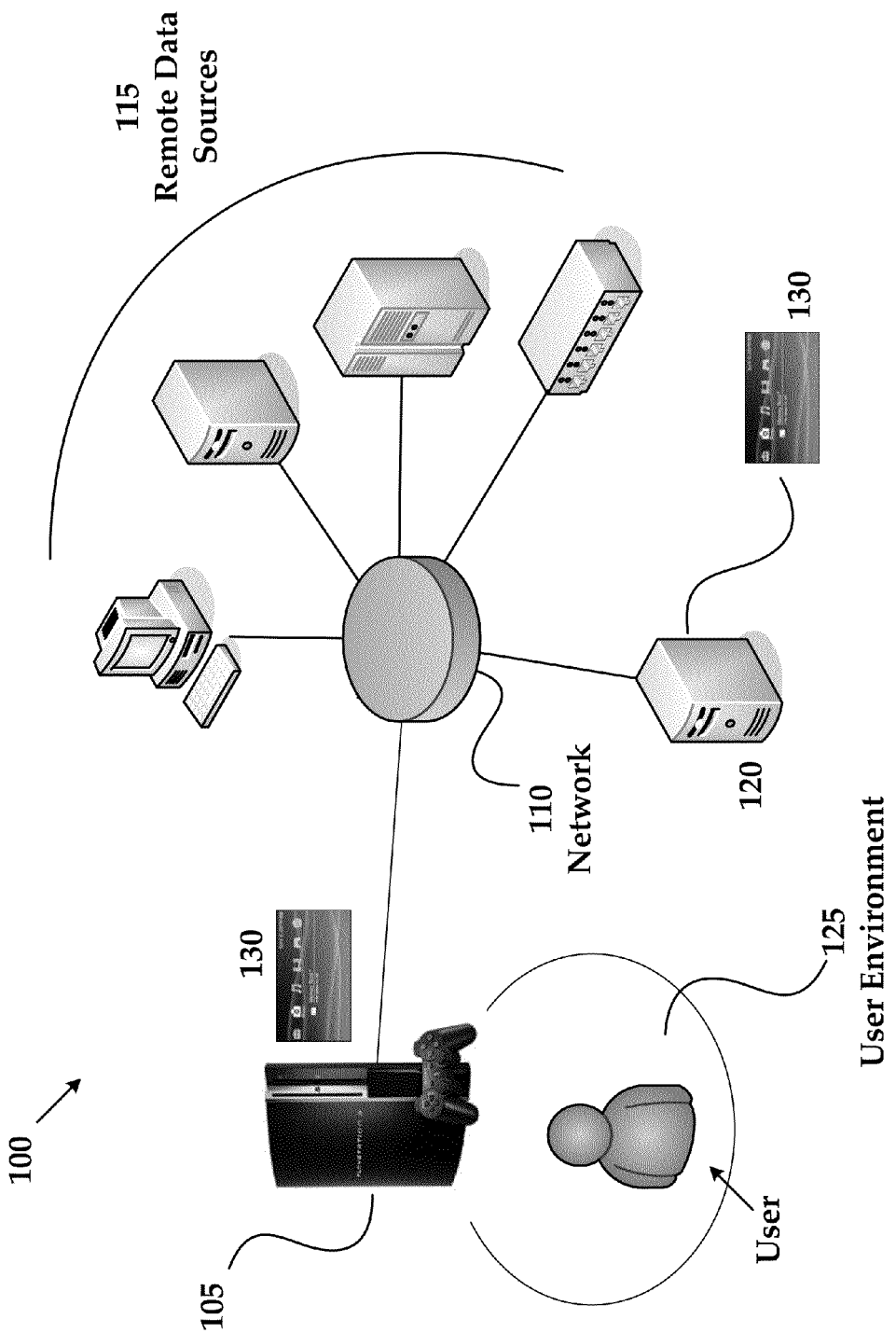
FIG. 1 illustrates an environment for providing an intelligent user interface that evolves based on learned idiosyncrasies and collected data of a user.

FIG. 1 illustrates an environment 100 for providing an intelligent user interface that evolves based on learned idiosyncrasies and collected data of a user. As depicted, the environment 100 includes a user device 105 in communication with a network 110. Remote data sources 115 and an optional server 120 are also in communication with the network 110. The network 110 facilitates communication between the user device 105, the remote data sources 115, the server 120, and any other devices communicatively coupled with the network 110. The user device 105, the remote data sources 115, and the server 120 include the requisite network interfaces, memory, and processing components as may be required to interact with one another via the network 110. User environment 125 includes an area that surrounds the user device 105 and a user thereof. Such an area could, for example, be a living room.

Both the user device 105 and the server 120 are shown as including an intelligent user interface system 130, however, the intelligent user interface system 130 may reside entirely in one device or may be distributed across two or more networked devices. The intelligent user interface system 130 is described in further detail in connection with FIG. 2. Environment 100 may include many devices such as the user device 105 and the server 120 in communication via the network 110.

The user device 105 can facilitate presentation of an intelligent user interface by way of the intelligent user interface system 130. While the user device 105 is depicted in FIG. 1 as housing the intelligent user interface system 130, the user device 105 may access via the network 110 an instance of the intelligent user interface system 130 residing on a remote computer such as the server 120. Similarly, the user device 105 may execute certain components of the intelligent user interface system 130 locally and access other components remotely via the network 110.

The user device 105 may include any portable consumer electronics device such as a smart phone, portable media playback device, or gaming device. Examples of the user device 105 include portable gaming devices such as a PSP™ and PSP Go from Sony Computer Entertainment Inc. The user device 105 may also include car stereos, e-book readers, and portable computers. The user device 105 may include one or more integrated output devices for presenting media or may also allow for an external coupling to the same (e.g., a display and speakers).

The user device 105 may also include any consumer electronics not specifically designed for portability. Examples of the user device 105 include a home entertainment system such as the PlayStation®3 available from Sony Computer Entertainment Inc. or more limited game hardware platforms of a different albeit inferior manufacture than those offered by Sony Computer Entertainment. Further examples of consumer electronics devices include various home theater components such as a Digital Versatile Disc (DVD) player, a Blu-Ray Disc player, a Digital Video Recorder, set-top cable boxes, and personal computers. The user device 105 may include one or more integrated output devices for presenting media or be coupled to the same.

The remote data sources 115 include any third-party server or database. Third-party servers may host services such as email and instant messaging services, banks and other financial institutions, social-networking websites, new sources, RSS feeds, and other websites. The remote data sources 115 can also include other devices similar to the user device 105.

The environment 100 can optionally include the server 120. The server 120 can store data associated with an instance of the intelligent user interface system 130 residing on the user device 105. The server 120 can also include the intelligent user interface system 130 to facilitate generation of an intelligent user interface to be presented by the user device 105. In such a case, the user device 105 may access an instance of the intelligent user interface system 130 being executed by the server 120 via the network 110. Furthermore, the server 120 can execute certain components of the intelligent user interface system 130 locally, while other components are executed by the user device 105.

Figure 2:
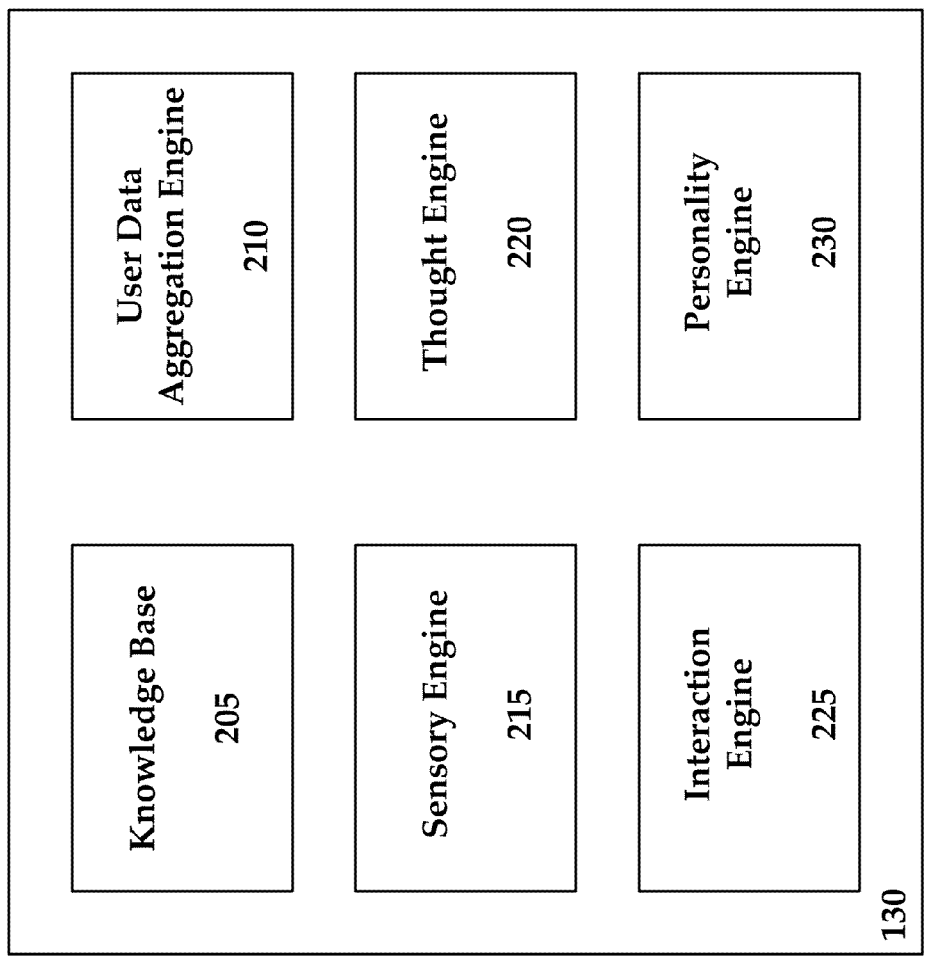
FIG. 2 is a block diagram of an exemplary intelligent user interface system that may be invoked in the environment illustrated in FIG. 1.

FIG. 2 is a block diagram of the exemplary intelligent user interface system 130 that may be invoked in the environment 100 illustrated in FIG. 1. As illustrated in FIG. 2, the intelligent user interface system 130 includes a knowledge base 205, a user data aggregation engine 210, a sensory engine 215, a thought engine 220, an interaction engine 225, and a personality engine 230. The individual program components and applications making up engines and modules of the intelligent user interface system 130 may be stored in memory of devices such as the user device 105 or the server 120. The intelligent user interface system 130 and its constituent engines and modules can be executed by a processor to effectuate respective functionalities attributed thereto. The intelligent user interface system 130 may be composed of more or fewer engines/modules or combinations of the same and still fall within the scope of the present invention. For example, the functionalities of the interaction engine 225 and the functionalities of the personality engine 230 may be combined into a single engine or module.

The knowledge base 205 can be a database that is configured to store learned idiosyncrasies and collected data of the user. Generally, learned idiosyncrasies are descriptive of individualizing qualities or characteristics of a particular user. The learned idiosyncrasies may account for certain eccentricities or peculiarities by identified habits and rituals of the user. Collected data of the user can encompass any information associated with the user. For example, collected data can include various facts about the user such as who they are, where they come from, and what they are interested in. The collected data may also include an index of user data stored locally or remotely such as game data, browser history, social network profile data, contacts, calendar events, media files, and so forth. Such learned idiosyncrasies and collected data may be regularly obtained by other constituent components of the intelligent user interface system 130 such that the knowledge base 205 is kept up to date. The learned idiosyncrasies and collected data stored by the knowledge base 205 can be accessed by other constituent component of the intelligent user interface system 130.

The knowledgebase is developed through cataloging local data associated with a user, collecting remote data associated with the user, recording information associated with verbal input received from the user, tracking acts performed by the user to determine user idiosyncrasies, and updating the knowledgebase with the cataloged local data, the collected remote data, the recorded information, and the user idiosyncrasies; and providing the updated knowledgebase to a component of the user interface. This particular method is illustrated in FIG. 6.

Figure 6:
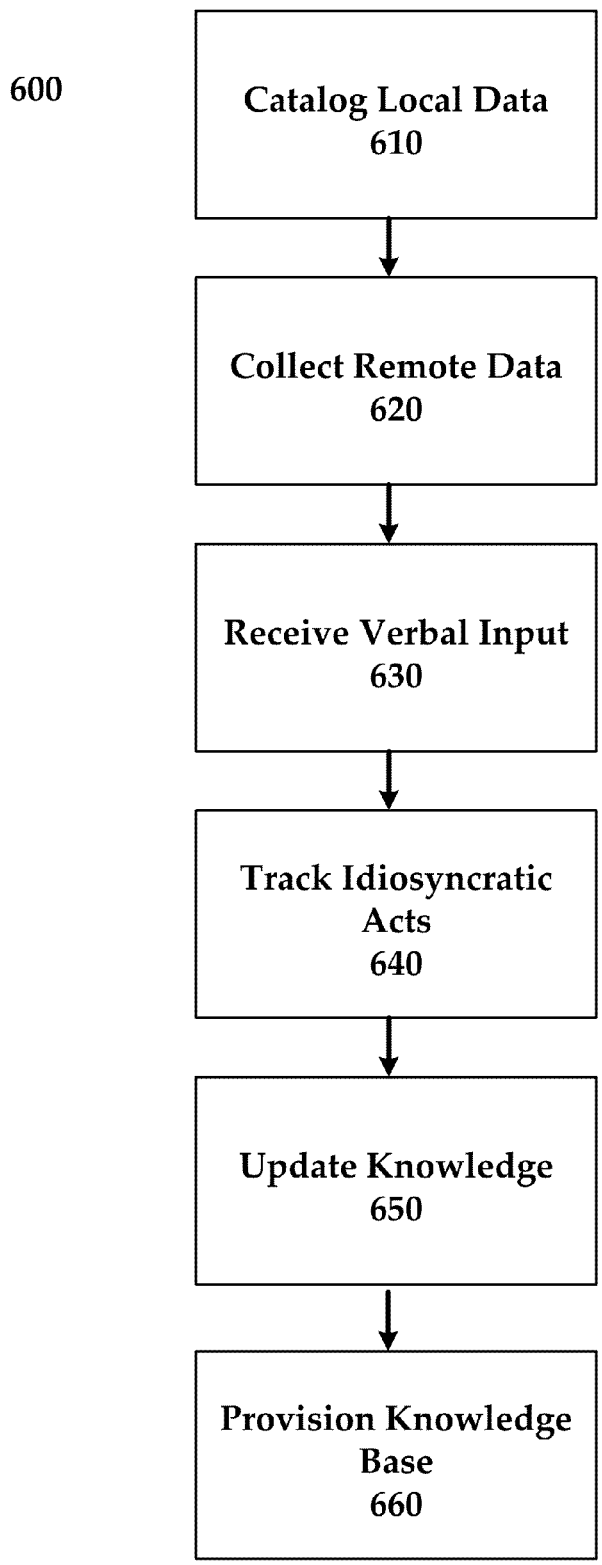
FIG. 6 is a method for developing a knowledgebase associated with a user interface.

Cataloging the local data, as addressed in step 610 of FIG. 6, may include cataloging locally accessible media. Cataloging the local data may alternatively include cataloging purchases that were made in conjunction with a system executing the instructions. Cataloging may also be inclusive of cataloging trophies, a browser history, devices in communication with a system developing the knowledgebase, cataloging available services, calendar events, friends of the user, and geographical location history. Collection of remote data, in turn and as addressed in step 620 of FIG. 6, may include indexing subscriptions of the user, indexing textual communication by the user, indexing information from third-party accounts associated with the user, and indexing information associated with other users having a relationship with the user.

The collection of information associated with verbal input (step 630 of FIG. 6) is inclusive of performing speech recognition to generate a transcription of verbal input and performing voice recognition to determine the identity of a speaker. Verbal input may identify characteristics of the user or interests of the user. The tracking of various idiosyncratic act of a user (step 640 of FIG. 6) may include tracking the geographical location history of the user, correlating times and dates with the geographical location history of the user, tracking activities in which the user participates, correlating times and dates with the activities, and tracking information associated with communication partners of the user. The information associated with the communication partners includes times and dates of communications between the user and the communication partners.

The user data aggregation engine 210 is executable to update the knowledge base 205 with information associated with the user. Updating the knowledge base may include cataloging local data associated with a user such as locally stored media and calendar events. Collecting remote data associated with the user such as memberships and purchase information may also be part of updating the knowledge base 205. The user data aggregation engine 210 can also be executed to record information associated with verbal input received from the user and to track acts performed by the user to determine user idiosyncrasies.

The sensory engine 215 can be executed to obtain information from the user environment 125 during learning of idiosyncrasies and/or collection of data. Examples of such information include visual or audible information. By being coupled to a microphone or array of microphones and/image sensing device or camera, data concerning the user environment 125 may be collected and processed by the sensory engine 215. This information could include the sound of a door opening at a particular time of day, which would indicate a user arriving home whereby the system may then engage in the offering of thought-based statements (e.g., "welcome home"). Camera data such as an image of the user could likewise invoke a thought-based statement conversation particular to a given user or conversation specific to a particular time of day based on light levels (e.g., "good evening"). The position of a user in the room or with respect to an input gathering device or in the real-world in general may be gathered using GPS, triangulation, cellular base station, or other location based information. Location information may be derived from other sources not traditionally associated with location identification but nevertheless indicative of the same (e.g., a debit card charge at a restaurant having a particular restaurant). The sensory engine 215 is described in further detail in connection with FIG. 2.

Execution of the thought engine 220 can generate thought-based statements based at least in part on the knowledge base 205 and the information from the user environment 125 obtained through execution of the sensory engine 215. The thought-based statements serve to invoke or respond to subsequent actions of the user. An example of a thought-based statement might be "welcome home, would you like me to play some music" or "it is currently 6 PM, would you like me to suggest a restaurant for dinner?" The thought engine 220 is described in further detail in connection with FIG. 4.

The interaction engine 225 is executable to present an intelligent user interface and to allow for interaction with the user based at least in part on the thought-based statements generated through execution of the thought engine 220. The intelligent user interface can include a number of form factors. For example, the intelligent user interface may present a visual image of face such that the interaction is akin to having a conversation with another real person. The interface could also be a character including a real-person (e.g., an avatar generated to appear similar to that of a person or randomly generated persona), a cartoon character (e.g., Homer Simpson), an animal (e.g., a talking dog) or other object (e.g., a blinking eye or giant lips). The interface could also be a touch screen, menu, or other data entry mechanism. The interaction engine 225 is described in further detail in connection with FIG. 5.

The personality engine 230 can be executed to develop personality nuances of the intelligent user interface that affect the interaction between the user and the intelligent user interface. Such personality nuances may include a particular sense of humor, inside knowledge of the user, an inside joke, a particular tone, and facial expressions. The personality engine 230 is described in further detail in connection with FIG. 8.

Figure 3:
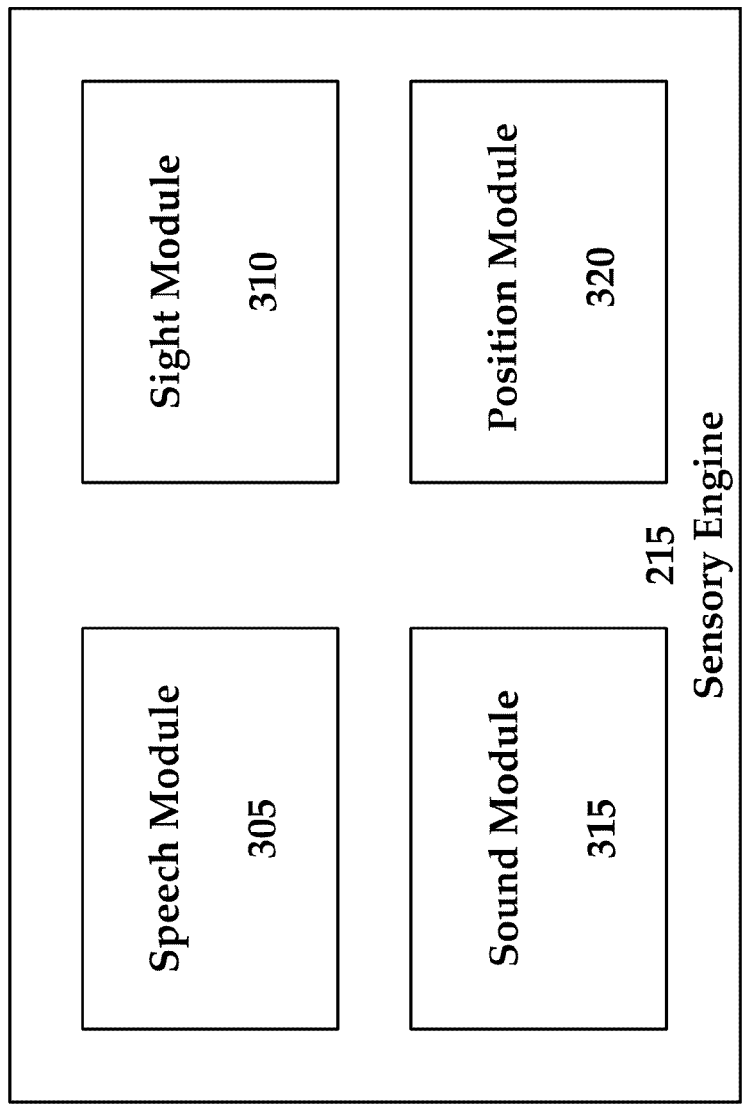
FIG. 3 is a block diagram of an exemplary sensory engine that may be included in the intelligent user interface system.

FIG. 3 is a block diagram of the exemplary sensory engine 215 that may be included in the intelligent user interface system 130. As mentioned in connection with FIG. 2, the sensory engine 215 can be executed to obtain information from the user environment 125 during learning of idiosyncrasies and/or collection of data. The sensory engine 215, as illustrated in FIG. 3, includes a speech module 305, a sight module 310, a sound module 315, and a position module 320. The individual program components and applications making up modules of the sensory engine 215 may be stored in memory of devices such as the user device 105 or the server 120. The constituent modules of the sensory engine 215 can be executed by a processor to effectuate respective functionalities attributed thereto. The sensory engine 215 may be composed of more or fewer modules or combinations of the same and still fall within the scope of the present invention.

The speech module 305 can be executed to decipher detected speech from the user. The speech module 305 may utilize Hidden Markov Models (HMM). HMM output a sequence of symbols or quantities. The speech signal can be viewed as a piecewise stationary signal or a short-time stationary signal whereby speech can be approximated as a stationary process allowing the speech to be thought of as a Markov model for stochastic processes. HMMs are popular in that they can be trained automatically and are simple and computationally feasible to use. The speech module 305 may also use Viterbi algorithms, acoustic and language model information, finite state transducers, and other speech recognition techniques.

The sight module 310 is executable to optically detect a body part of the user. For example, the sight module 310 can be executed to detect a hand of the user in order to detect a manual gesture. The sight module 310 may also be executed to detect the face of the user such as to perform facial recognition.

In the latter example, a facial recognition algorithm may identify faces by extracting landmarks, or features, from an image of the subject's face such as the relative position, size, and/or shape of the eyes, nose, cheekbones, and jaw. These features are then used to search for other images with matching features. Other algorithms normalize a gallery of face images and then compress the face data, only saving the data in the image that is useful for face detection; a probe image is then compared with the face data. Recognition algorithms can generally be divided into the geometric, which look at distinguishing features or photometric, which is a statistical approach that distills an image into values and comparing the values with templates to eliminate variances. Other techniques include three-dimensional recognition that uses 3-D sensors to capture information about the shape of a face to identify distinctive features and skin texture analysis, which uses the visual details of the skin and turns the unique lines, patterns, and spots into a mathematical space.

Optical information of the user environment 125 can be obtained using a camera communicatively coupled or integral with the user device 105, as described in connection with FIG. 9.

Execution of the sound module 315 allows a response to an audio signal in the user environment 125 to be provided.

Audio signals in the user environment 125 can be detected using a microphone integral or communicatively coupled with the user device 105, as described in connection with FIG. 9. For example, the sound module 315 might identify a sudden sound against a previously existing background of silence as might occur with the opening of a door in a previously empty room. That sound might indicate the presence of a user.

The position module 320 can be executed to determine the location and/or motion of the user. Positional information indicative of the location and motion of the user can be obtained through GPS and other triangulation techniques, including base stations. For example, GPS information can be obtained using a GPS device communicatively coupled or integral with the user device 105, as described in connection with FIG. 9.

Figure 4:
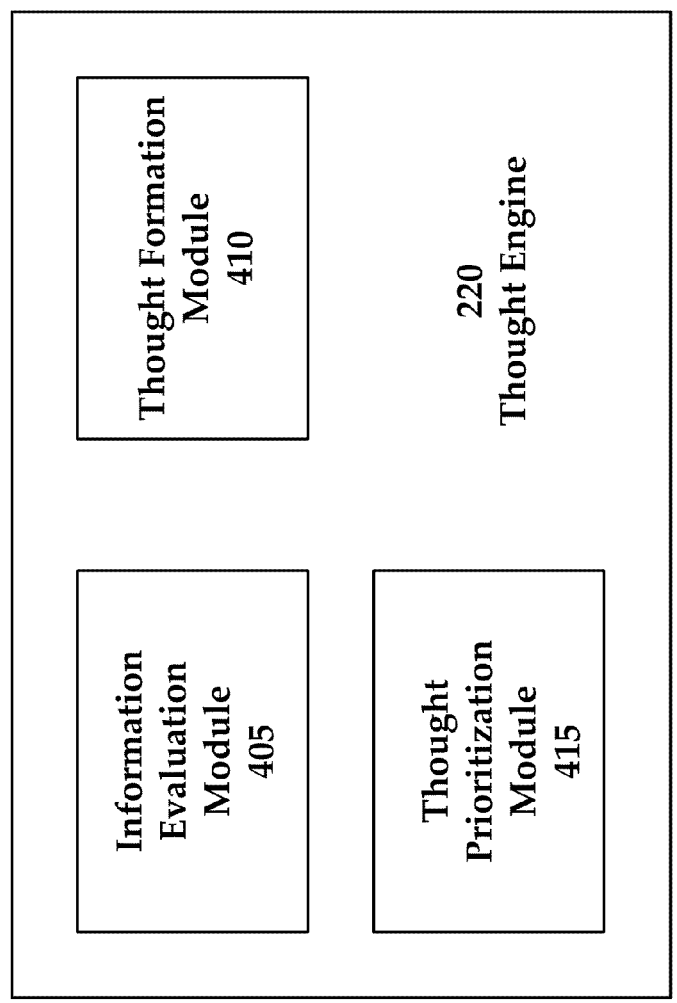
FIG. 4 is a block diagram of an exemplary thought engine that may be included in the intelligent user interface system.

FIG. 4 is a block diagram of the exemplary thought engine 220 that may be included in the intelligent user interface system 130. As mentioned in connection with FIG. 2, the thought engine can be executed to generate thought-based statements based at least in part on the knowledge base 205 and the information from the user environment 125 obtained through execution of the sensory engine 215. As illustrated in FIG. 4, the thought engine 220 includes an information evaluation module 405, a thought formation module 410, and a thought prioritization module 415. The individual program components and applications making up modules of the thought engine 220 may be stored in memory of devices such as the user device 105 or the server 120. The constituent modules of the thought engine 220 can be executed by a processor to effectuate respective functionalities attributed thereto. The thought engine 220 may be composed of more or fewer modules or combinations of the same and still fall within the scope of the present invention.

The information evaluation module 405, when executed, evaluates all or some portion of available information associated with the user. This can entail evaluation of the knowledge base 205 as well as the information from the user environment 125 obtained though execution of the sensory engine 215. Information evaluation module 405 aggregates all available information relevant to a particular scenario to generate parameters that might drive a subsequent thought based statement generated by the thought formation module 410. Information evaluation module 405 may access knowledge base 205 to recognize certain patterns of behavior in light of current sensory information. For example, if the knowledge base 205 reflects that a particular user arrives home Monday through Friday at approximately 5:30 PM, the presence of sound corresponding to an opening door at 5:24 PM on a Thursday may similarly indicate the arrival of that user. With that information having been recognized by information evaluation module 405, the thought formation module 410 may then formulate an appropriate thought statement. Information evaluation module 405 may similarly recognize that two users typically arrive home at the same time and require additional information such as recognizing the voice of a user or processing image information of the user. In this way, the thought formation module 410 may then generate the appropriate greeting (e.g., "Hello, Will" or "Hello, Holly").

The thought formation module 410 can be executed to formulate the thought-based statements in response to an evaluation of the knowledge base 205 and the information from the user environment 125 as undertaken by information evaluation module 405. The thought formation module 410 may then issue appropriate thought-based statements such as "Good evening, Will" when clock time indicates that it is 5:30 PM and Will typically arrives home at 5:30, a camera having processed image data confirming that Will is, in fact, home rather than his roommate or girlfriend. Similarly, the thought formation module 410 may recognize, in light of parameters from the information evaluation module 405, that any of those three persons might have entered into the room and issue a more generic greeting such as "Good evening, who has arrived home?" in order to prompt an informative response from the user—that response also being processed by information evaluation module 405.

The thought prioritization module 415 is executable to prioritize the thought-based statements based on importance. For example, the thought prioritization module 415 may indicate that of three thought-based statements identified as being appropriate for the arrival of a user into the room at 5:30 PM on a Friday (as indicated by parameters generated by the information evaluation module 405) that "Good evening, welcome home" should be rendered before statements such as "would you like me to make a dinner suggestion?" or "would you like me to play some music?" If the entering user states, "thank you, I'm hungry, any suggestions for dinner" in response to the "welcome home greeting," then the prioritization module may indicate that the next based statement should be "would you like me to make a dinner suggestion?" rather than inquiring as to music and launching a library of available music or even inquiring into a particular song or artist. Prioritization is dependent upon the context of any given situation and history related to that situation as determined by the information evaluation module 405.

Figure 5:
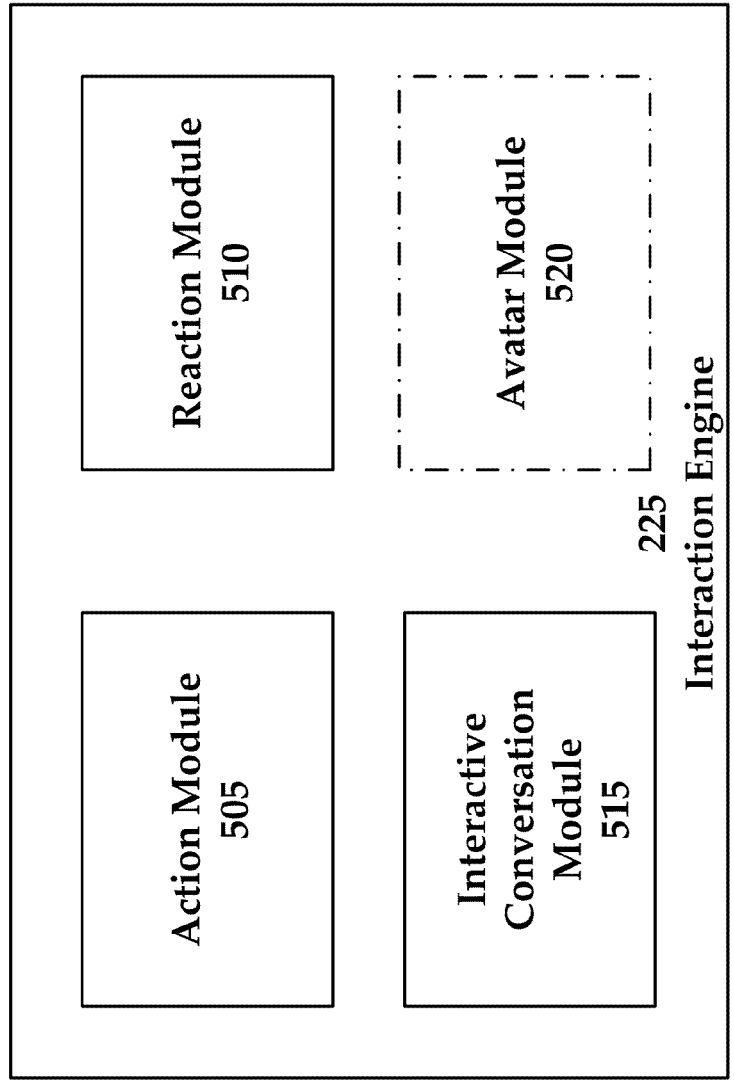
FIG. 5 is a block diagram of an exemplary interaction engine that may be included in the intelligent user interface system.

FIG. 5 is a block diagram of the exemplary interaction engine 225 that may be included in the intelligent user interface system 130. As mentioned in connection with FIG. 2, the interaction engine 225 can be executed to present an intelligent user interface and to allow for interaction with the user based at least in part on the thought-based statements generated through execution of the thought engine 220. The interaction engine 225 depicted in FIG. 5 includes an action module 505, a reaction module 510, an interactive conversation module 515, and an optional avatar module 520. The individual program components and applications making up modules of the interaction engine 225 may be stored in memory of devices such as the user device 105 or the server 120. The constituent modules of the interaction engine 225 can be executed by a processor to effectuate respective functionalities attributed thereto. The interaction engine 225 may be composed of more or fewer modules or combinations of the same and still fall within the scope of the present invention.

The action module 505 is executable to perform actions based on the thought-based statements. For example, if a thought-based statement suggests the playing of music, the action module 505 may launch a music library and indicate available songs and artists. Similarly, if a statement suggests restaurants, a map may be launched indicating location, reviews, or means for making a reservation.

The reaction module 510 can be executed to perform reactions to information obtained from the user environment 125. If camera data indicates that the light level in the room has dipped, the reaction module 510 can trigger the activation of room lighting if the system is coupled to a light management system. Similarly, if sound volume dips in the room, then the volume associated with music being played by the system will also dip to avoid it being too loud. In another example, if the phone rings (as indicated by the detected sound of a ringer or through a VOIP connection coupled to the system), the reaction module 510 may pause playback of a movie or game and result in the generation of a thought based statement inquiring as to whether the call should be answered.

The interactive conversation module 515 is executable to provide verbal responses to verbal input by the user. For example, if a user requests music, then the interactive conversation module 515 may respond, "I'd be happy to comply—is there a particular type of music you would like to listen to?" By working in conjunction with other modules and the knowledge base 205, the interactive conversation module 515 may determine that a user likes a particular genre of music on particular days or at particular times and suggest playback of that particular genre in a similar situation.

Execution of the optional avatar module 520 allows presentation of an avatar to the user as a part of the intelligent user interface. Examples of avatars are disclosed in U.S. patent application Ser. No. 12/887,397 entitled "Evolution of a User Interface Based on Learned Idiosyncrasies and Collected Data of a User," the disclosure of which has previously been incorporated herein by reference.

FIG. 6 is a method 600 for developing a knowledgebase associated with a user interface. In step 610, local data associated with a user is cataloged. In step 620, remote data associated with the user is collected. In step 630, information associated with verbal input form a user is received and recorded. Acts performed by the user to determine idiosyncrasies are tracked in step 640. The knowledge is then updated in step 650 with cataloged local data, collected remote data, recorded information, and the user idiosyncrasies. The updated knowledge base is provided to one or more components of the user interface at step 660.

Figure 7:
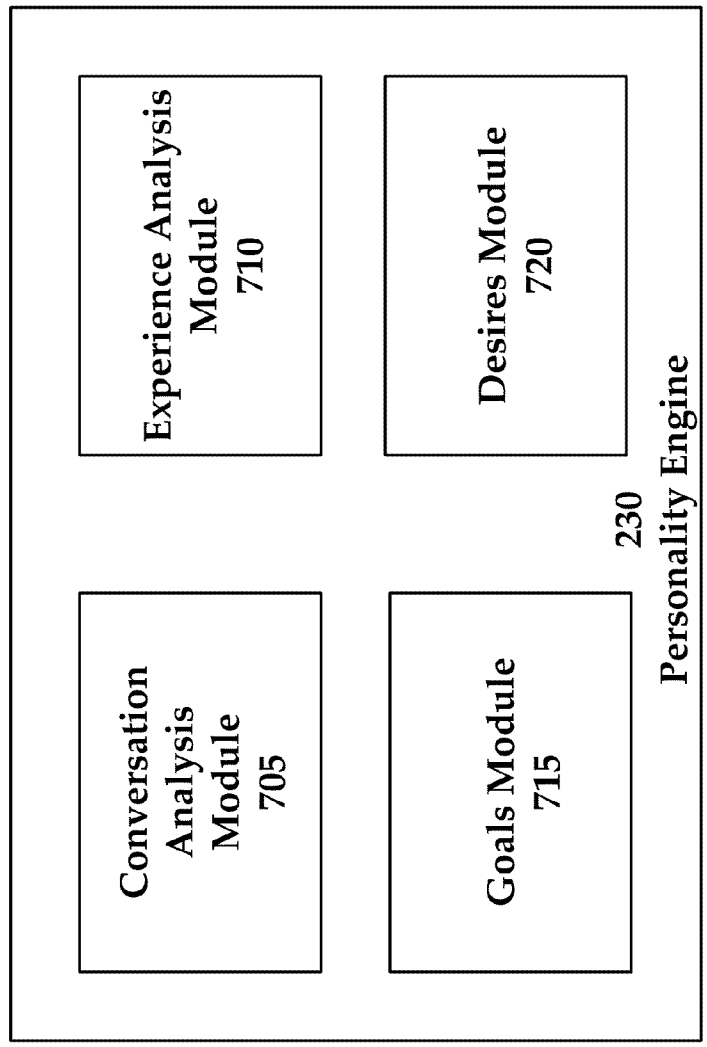
FIG. 7 is a block diagram of an exemplary personality engine that may be included in the intelligent user interface system.

FIG. 7 is a block diagram of the exemplary personality engine 230 that may be included in the intelligent user interface system 130. As mentioned in connection with FIG. 2, the personality engine 230 can be executed to develop personality nuances of the intelligent user interface that affect the interaction between the user and the intelligent user interface. As illustrated in FIG. 7, the personality engine 230 includes a conversation analysis module 705, an experience analysis module 710, a goals module 715, and a desires module 720. The individual program components and applications making up modules of the personality engine 230 may be stored in memory of devices such as the user device 105 or the server 120. The constituent modules of the personality engine 230 can be executed by a processor to effectuate respective functionalities attributed thereto. The personality engine 230 may be composed of more or fewer modules or combinations of the same and still fall within the scope of the present invention.

The conversation analysis module 705 can be executed to analyze past verbal input by the user. The generated thought-based statements may be based in part the analysis of the past verbal input. For example, certain statements ("I had a lousy day") may be indicative of mood or present feeling, which may be used to present certain options if similar conversational interactions are identified in the future.

The experience analysis module 710 is executable to analyze past interactions between the user and the user device 105. The generated thought-based statements can be based in part on the analysis of the past interactions. For example, a logic tree might be developed that indicates a particular flow of conversation results in a particular set of discussion options (e.g., an inquiry as to food leads to offering up a suggestion, which then leads to type of food, followed by proximity, and ultimately the availability of reservations or take out).

Execution of the goals module 715 allows formation of goals of the intelligent user interface. The generated thought-based statements may be based in part on the goals. The goals module 715 may, for example, work in conjunction with other modules to identify an ultimate result to be generated from a conversation. For example, if a user inquires as to dinner suggestions, the goals module 715 may recognize that it ultimately needs to find a restaurant that is open, within driving distance (or some other parameter, which may in and of itself be a goal), of a particular type of food and have reservations for a particular number of people at a particular time. AS a result of recognizing these goals, the requisite thought-based statements may be generated as to generate the appropriate responsive answers. What constitutes a goal for any given conversation may be recognized over time from information gathered by the knowledge base 205.

The desires module 720 can be executed to form desires of the intelligent user interface. The generated thought-based statements can be based in part on the desires. For example, if the system recognizes that a user is in a bad mood, then desires module 720 may seek to arrive at some end result that cheers up the user. This may involve suggesting a particular activity, television show, or contacting a friend by phone. Like all modules of the present system, interaction with other modules and data sources may be necessary to properly identify a state of mind or being of a user and that a particular desire or goal is appropriate.

Figure 8:
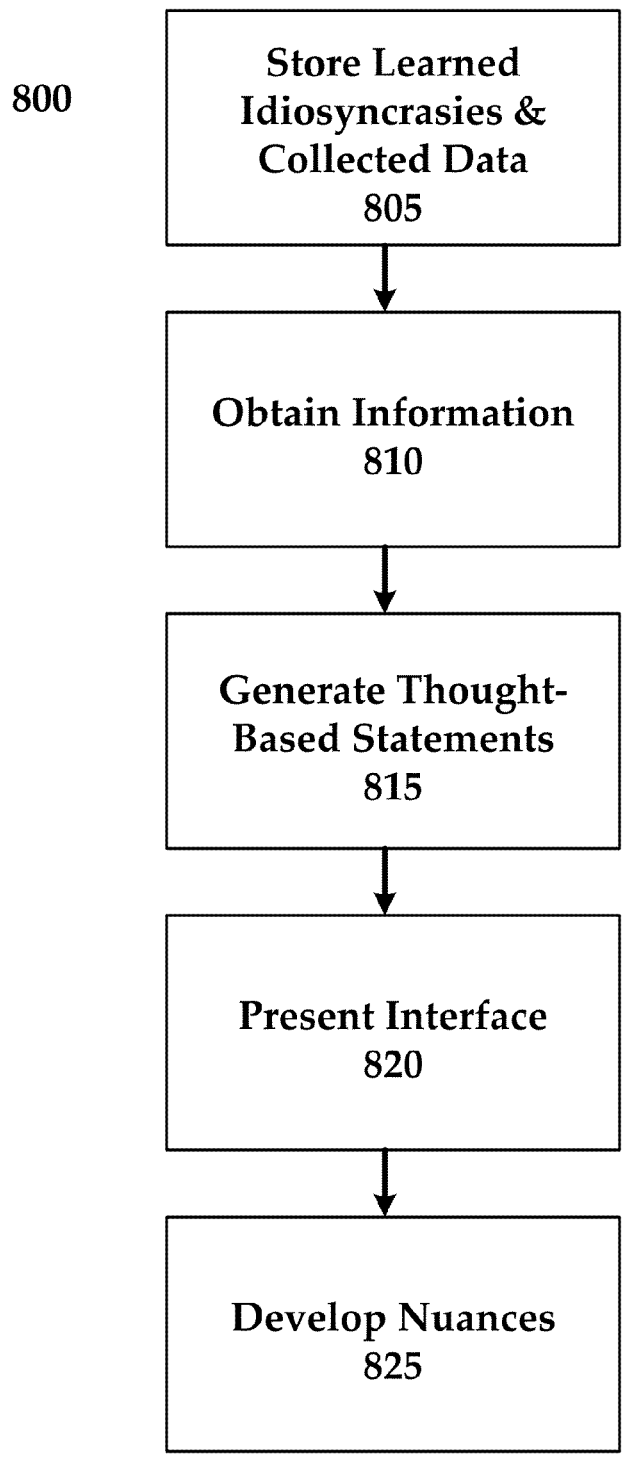
FIG. 8 is a flowchart illustrating an exemplary method for providing an intelligent user interface that evolves based on learned idiosyncrasies and collected data of a user.

FIG. 8 is a flowchart illustrating an exemplary method 800 for providing an intelligent user interface that evolves based on learned idiosyncrasies and collected data of a user. The steps of the method 800 may be performed in varying orders. Furthermore, steps may be added or subtracted from the method 800 and still fall within the scope of the present technology. The methodology illustrated in FIG. 8 may be embodied on a computer-readable storage medium and executable by a processing device at any one of the devices illustrated in FIG. 1.

In step 805, learned idiosyncrasies and collected data of the user are stored in the knowledge base 205. Step 805 can be performed in conjunction with execution of the user data aggregation engine 210.

In step 810, information is obtained from the surrounding environment of the user (e.g., the user environment 125) during learning of idiosyncrasies or collection of data. Step 810 can be performed by way of execution of the sensory engine 215.

In step 815, thought-based statements are generated based at least in part on the knowledge base 205 and the information from the environment surrounding the user during learning of idiosyncrasies or collection of data. As mentioned herein, the thought-based statements serve to invoke or respond to subsequent actions of the user. The thought engine 220 can be executed to perform step 815.

In step 820, the user interface is presented and interaction with the user is allowed therewith based at least in part on the thought-based statements. Step 820 can be performed through execution of the interaction engine 225.

In step 825, personality nuances of the user interface are developed that affect the interaction between the user and the user interface. The personality engine 230 can be executed to perform step 825.

Figure 9:
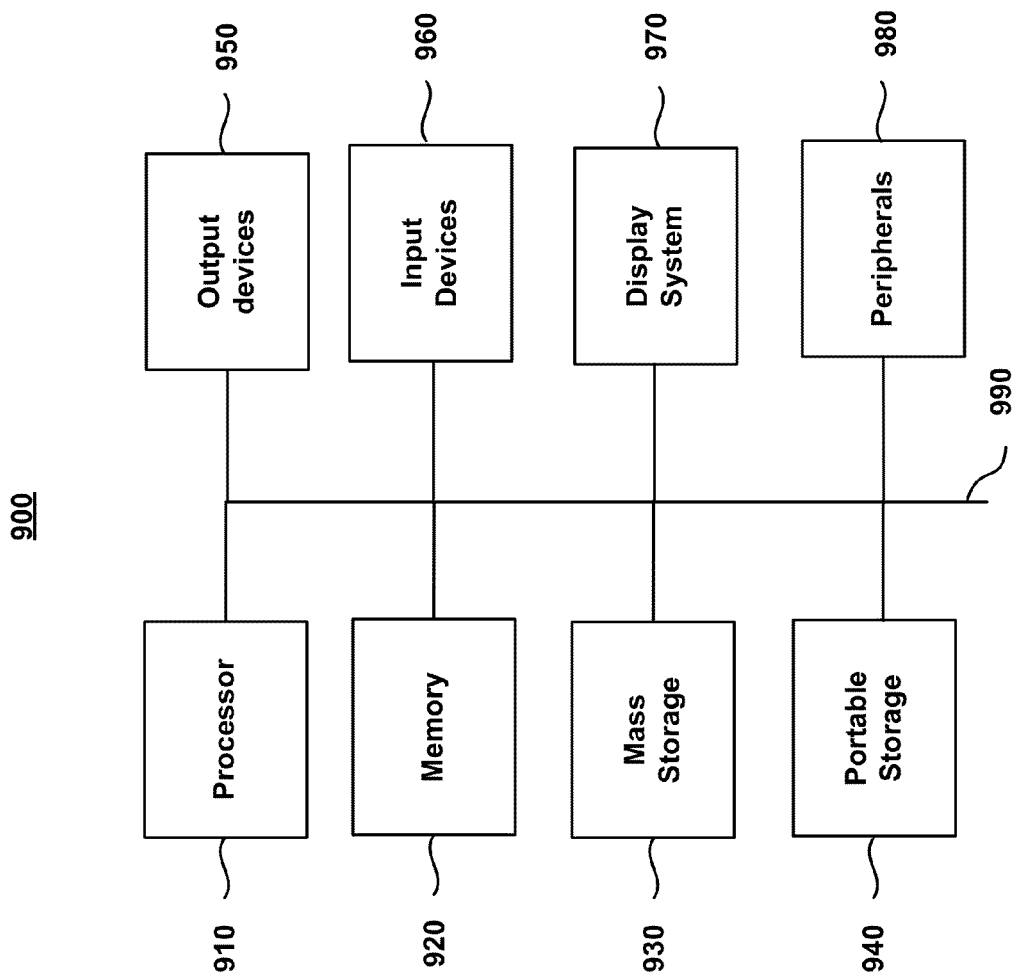
FIG. 9 is a block diagram illustrating an exemplary device that may be used to implement an embodiment of the present invention.

FIG. 9 is a block diagram illustrating an exemplary device 900 that may be used to implement an embodiment of the present technology. The device 900 may be implemented in the contexts of the likes of the user device 105 and the server 120. The device 900 of FIG. 9 includes one or more processors 910 and main memory 920. Main memory 920 stores, in part, instructions and data for execution by processor 910. Main memory 920 can store the executable code when in operation. The device 900 of FIG. 9 further includes a mass storage device 930, portable storage device(s) 940, output devices 950, user input devices 960, a display system 970, and peripheral devices 980.

The components shown in FIG. 9 are depicted as being connected via a single bus 990. The components may be connected through one or more data transport means. The processor 910 and the main memory 920 may be connected via a local microprocessor bus, and the mass storage device 930, peripheral device(s) 980, portable storage device 940, and display system 970 may be connected via one or more input/output (I/O) buses.

Mass storage device 930, which may be implemented with a magnetic disk drive or an optical disk drive, is a non-volatile storage device for storing data and instructions for use by processor 910. Mass storage device 930 can store the system software for implementing embodiments of the present invention for purposes of loading that software into main memory 920.

Portable storage device 940 operates in conjunction with a portable non-volatile storage medium, such as a floppy disk, compact disk, digital video disc, or USB storage device, to input and output data and code to and from the device 900 of FIG. 9. The system software for implementing embodiments of the present invention may be stored on such a portable medium and input to the device 900 via the portable storage device 940.

Input devices 960 provide a portion of a user interface. Input devices 960 may include an alpha-numeric keypad, such as a keyboard, for inputting alpha-numeric and other information, or a pointing device, such as a mouse, a trackball, stylus, or cursor direction keys. Additionally, the device 900 as shown in FIG. 9 includes output devices 950. Suitable output devices include speakers, printers, network interfaces, and monitors.

Display system 970 may include a liquid crystal display (LCD) or other suitable display device. Display system 970 receives textual and graphical information, and processes the information for output to the display device.

Peripheral device(s) 980 may include any type of computer support device to add additional functionality to the computer system. Peripheral device(s) 980 may include a modem, a router, a camera, a microphone, and a GPS receiver. Peripheral device(s) 980 can be integral or communicatively coupled with the device 900.

The components contained in the device 900 of FIG. 9 are those typically found in computing systems that may be suitable for use with embodiments of the present invention and are intended to represent a broad category of such computing components that are well known in the art. Thus, the device 900 of FIG. 9 can be a home entertainment system, personal computer, hand-held computing device, telephone, mobile computing device, workstation, server, minicomputer, mainframe computer, or any other computing device. The device 900 can also include different bus configurations, networked platforms, multi-processor platforms, etc. Various operating systems can be used including Unix, Linux, Windows, Macintosh OS, Palm OS, webOS, Android, iPhone OS, and other suitable operating systems.

It is noteworthy that any hardware platform suitable for performing the processing described herein is suitable for use with the technology. Computer-readable storage media refer to any medium or media that participate in providing instructions to a central processing unit (CPU), a processor, a microcontroller, or the like. Such media can take forms including, but not limited to, non-volatile and volatile media such as optical or magnetic disks and dynamic memory, respectively. Common forms of computer-readable storage media include a floppy disk, a flexible disk, a hard disk, magnetic tape, any other magnetic storage medium, a CD-ROM disk, digital video disk (DVD), any other optical storage medium, RAM, PROM, EPROM, a FLASHEPROM, any other memory chip or cartridge.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A computer-implemented method for developing a knowledgebase associated with a user interface, the method comprising:
   executing instructions stored in memory to:
      catalog local data associated with a user, wherein executing instructions to catalog the local data includes cataloging purchases that were made in conjunction with a system executing the instructions,
      collect remote data associated with the user,
      record information associated with verbal input received from the user,
      track acts performed by the user to determine user idiosyncrasies, and
      update the knowledgebase with the cataloged local data, the collected remote data, the recorded information, and the user idiosyncrasies; and
   providing the updated knowledgebase to a component of the user interface.

2. The method of claim 1, wherein executing instructions to catalog the local data further includes cataloging locally accessible media.

3. The method of claim 1, wherein executing instructions to catalog the local data further includes cataloging trophies stored by a system executing the instructions.

4. The method of claim 1, wherein executing instructions to catalog the local data associated with a user further includes cataloging a browser history of a system executing the instructions.

5. The method of claim 1, wherein executing instructions to catalog the local data associated with a user further includes cataloging devices that are in communication with a system executing the instructions.

6. The method of claim 1, wherein executing instructions to catalog the local data associated with a user further includes cataloging services that are available via a system executing the instructions.

7. The method of claim 1, wherein executing instructions to catalog the local data associated with a user further includes cataloging calendar events stored by a system executing the instructions.

8. The method of claim 1, wherein executing instructions to catalog the local data associated with a user further includes cataloging friends of the user identified by a system executing the instructions.

9. The method of claim 1, wherein executing instructions to catalog the local data associated with a user further includes cataloging geographical location history of a system executing the instructions.

10. The method of claim 1, wherein executing instructions to collect remote data associated with the user includes indexing subscriptions of the user.

11. The method of claim 1, wherein executing instructions to collect remote data associated with the user includes indexing textual communication by the user.

12. The method of claim 1, wherein executing instructions to collect remote data associated with the user includes indexing information from third-party accounts associated with the user.

13. The method of claim 1, wherein executing instructions to collect remote data associated with the user includes indexing information associated with other users having a relationship with the user.

14. The method of claim 1, wherein executing instructions to record information associated with the verbal input includes performing speech recognition to generate a transcription of verbal input.

15. The method of claim 1, wherein executing instructions to record information associated with the verbal input includes performing voice recognition to determine the identity of a speaker.

16. The method of claim 1, wherein the verbal input identifies characteristics of the user.

17. The method of claim 1, wherein the verbal input identifies interests of the user.

18. The method of claim 1, wherein executing instructions to track acts performed by the user includes tracking the geographical location history of the user.

19. The method of claim 18, wherein executing instructions to track acts performed by the user further includes correlating times and dates with the geographical location history of the user.

20. The method of claim 1, wherein executing instructions to track acts performed by the user includes tracking activities in which the user participates.

21. The method of claim 20, wherein executing instructions to track acts performed by the user further includes correlating times and dates with the activities.

22. The method of claim 1, wherein executing instructions to track acts performed by the user further includes tracking information associated with communication partners of the user.

23. The method of claim 22, wherein information associated with communication partners include times and dates of communications between the user and the communication partners.

24. A computer-implemented method for developing a knowledgebase associated with a user interface, the method comprising:
executing instructions stored in memory to:
catalog local data associated with a user, wherein executing instructions to catalog the local data includes catalog trophies stored by a system executing the instructions,
collect remote data associated with the user,
record information associated with verbal input received from the user,
track acts performed by the user to determine user idiosyncrasies, and
update the knowledgebase with the cataloged local data, the collected remote data, the recorded information, and the user idiosyncrasies; and
providing the updated knowledgebase to a component of the user interface.

25. The method of claim 24, wherein executing instructions to catalog the local data further includes cataloging locally accessible media.

26. The method of claim 24, wherein executing instructions to catalog the local data further includes cataloging purchases that were made in conjunction with a system executing the instructions.

27. The method of claim 24, wherein executing instructions to catalog the local data associated with a user further includes cataloging a browser history of a system executing the instructions.

28. The method of claim 24, wherein executing instructions to catalog the local data associated with a user further includes cataloging devices that are in communication with a system executing the instructions.

29. The method of claim 24, wherein executing instructions to catalog the local data associated with a user further includes cataloging services that are available via a system executing the instructions.

30. The method of claim 24, wherein executing instructions to catalog the local data associated with a user further includes cataloging calendar events stored by a system executing the instructions.

31. The method of claim 24, wherein executing instructions to catalog the local data associated with a user further includes cataloging friends of the user identified by a system executing the instructions.

32. The method of claim 24, wherein executing instructions to catalog the local data associated with a user further includes cataloging geographical location history of a system executing the instructions.

33. The method of claim 24, wherein executing instructions to collect remote data associated with the user includes indexing subscriptions of the user.

34. The method of claim 24, wherein executing instructions to collect remote data associated with the user includes indexing textual communication by the user.

35. The method of claim 24, wherein executing instructions to collect remote data associated with the user includes indexing information from third-party accounts associated with the user.

36. The method of claim 24, wherein executing instructions to collect remote data associated with the user includes indexing information associated with other users having a relationship with the user.

37. The method of claim 24, wherein executing instructions to record information associated with the verbal input includes performing speech recognition to generate a transcription of verbal input.

38. The method of claim 24, wherein executing instructions to record information associated with the verbal input includes performing voice recognition to determine the identity of a speaker.

39. The method of claim 24, wherein the verbal input identifies characteristics of the user.

40. The method of claim 24, wherein the verbal input identifies of the user.

41. The method of claim 24, wherein executing instructions to track acts performed by the user includes tracking the geographical location history of the user.

42. The method of claim 41, wherein executing instructions to track acts performed by the user further includes correlating times and dates with the geographical location history of the user.

43. The method of claim 24, wherein executing instructions to track acts performed by the user includes tracking activities in which the user participates.

44. The method of claim 43, wherein executing instructions to track acts performed by the user further includes correlating times and dates with the activities.

45. The method of claim 24, wherein executing instructions to track acts performed by the user includes tracking information associated with communication partners of the user.

46. The method of claim 45, wherein the information associated with the communication partners includes times and dates of communications between the user and the communication partners.

* * * * *